United States Patent [19]

Lewis

[11] 4,454,073

[45] Jun. 12, 1984

[54] N-[CARBOXYL(CARBAMOYL)CARBONYL]-AMINOMETHYL PHOSPHONIC ACIDS

[75] Inventor: Terence Lewis, Bracknell, England

[73] Assignee: Imperial Chemical Industries PLC, London, England

[21] Appl. No.: 362,276

[22] Filed: Mar. 26, 1982

[30] Foreign Application Priority Data

Apr. 16, 1981 [GB] United Kingdom ............... 81 12177

[51] Int. Cl.$^3$ .......................... C07F 9/38; A01N 57/20

[52] U.S. Cl. .................................. 260/501.21; 71/86; 71/87; 260/502.56; 260/940; 260/944; 260/984; 548/413

[58] Field of Search ............ 260/502.5 G, 944, 501.21

[56] References Cited

U.S. PATENT DOCUMENTS 4,094,928 6/1978 Gaertner .............................. 260/944

Primary Examiner—Anton H. Sutto
Attorney, Agent, or Firm—Cushman, Darby & Cushman

[57] ABSTRACT

Substituted methylphosphonic acids as herbicides.

4 Claims, No Drawings

N-[CARBOXYL(CARBAMOYL)CARBONYL]-AMINOMETHYL PHOSPHONIC ACIDS

This invention relates to substituted methylphosphonic acid derivatives useful as herbicides, and to herbicidal compositions and processes utilising them.

According to the present invention there are provided substituted methylphosphonic acid derivatives of the formula (I) or (II).

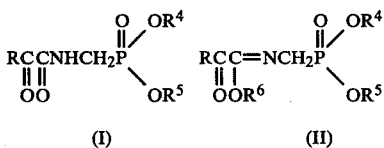

(I)                (II)

wherein R is (a) a group $R^1O$ wherein $R^1$ is hydrogen, a cation, or an ester radical; or (b) a group $R^2R^3N-$ wherein $R^2$ is hydrogen or an optionally substituted alkyl, alkenyl, or alkynyl group, and $R^3$ is hydrogen, an optionally substituted alkyl, alkenyl, alkynyl, or phenyl group, or an acyl group, or $R^2$ and $R^3$ together with the nitrogen atom to which they are attached, form a heterocyclic ring;

$R^4$ is hydrogen or a cation; $R^5$ is hydrogen, a cation or an alkyl group;

and $R^6$ is hydrogen, or an optionally substituted alkyl, alkenyl, or alkynyl radical.

When either $R^1$, $R^4$ or $R^5$ is a cation, it may be for example a metal cation or an ammonium or substituted ammonium cation. Metal cations include for example alkali metal cations (e.g. lithium, sodium and potassium) and alkaline earth metal cations (e.g. calcium and magnesium). Substituted ammonium cations include, for example, mono-, di-, tri- and tetra- alkyl substituted ammonium cations in which the alkyl group or groups may each contain for example from one to 20 carbon atoms (e.g. 1 to 6 carbon atoms) and which may optionally be substituted with one or more phenyl, halogen or hydroxy groups. Particular examples of substituted ammonium cations include ethylammonium, methylammonium, isopropylammonium, benzyltrimethyl ammonium, 2-hydroxyethylammonium and tri(2-hydroxyethyl)ammonium.

The applicants do not wish to be bound by any particular theory as to the mode of action of the compounds of the invention as herbicides. However, it is believed that compounds in which the group R is an $R^1O$ group wherein $R^1$ is an ester radical may well be hydrolysed in plant tissues to form the corresponding compound in which R is an OH group. The identity of the ester radical $R^1$ is therefore probably not critical to the herbicidal activity of the compounds, and a wide variety of ester radicals $R^1$ may be employed without losing the herbicidal activity of the compounds.

When $R^1$ is an ester radical, it may be for example an optionally substituted alkyl or cycloalkyl radical. The alkyl radical may contain for example from 1 to 20 (e.g. from 1 to 6) carbon atoms, and the cycloalkyl radical may for example contain from 3 to 6 carbon atoms. Examples of substituents which may be present in the alkyl or cycloalkyl radical include halogen (fluorine, chlorine, bromine or iodine); alkoxy (e.g. alkoxy of 1 to 6 carbon atoms) alkylthio (e.g. alkylthio of 1 to 6 carbon atoms); and optionally substituted phenyl (wherein the substituents may, for example, comprise one or more atoms of fluorine, chlorine, bromine or iodine or $C_1-C_6$ alkoxy, $CF_3$, $NO_2$, CN, or $C_1-C_6$ alkyl or alkenyl groups).

The ester radical $R^1$ may also be an alkenyl or alkynyl radical, optionally containing one or more substituents. Examples of substituents include those recited above for alkyl and cycloalkyl. The alkenyl or alkynyl radical may contain for example from 2 to 6 or more carbon atoms.

The ester radical $R^1$ may also be, for example an optionally substituted phenyl radical. Examples of substituents which may be present include alkyl (e.g. $C_1-C_6$ alkyl), alkenyl (e.g. $C_2-C_6$ alkenyl), alkoxy (e.g. $C_1-C_6$ alkoxy), alkylthio (e.g. $C_1-C_6$ alkylthio), alkylsulphinyl (e.g. $C_1-C_6$ alkylsulphinyl), alkanesulphonyl (e.g. $C_1-C_6$ alkanesulphonyl), nitro, cyano, carboxy, carbamoyl, alkoxycarbonyl (e.g. alkoxycarbonyl of 2-6 carbon atoms), haloalkyl (e.g. $CF_3$), and halogen (i.e. fluorine, chlorine, bromine or iodine).

When $R^2$ is a substituted alkyl, alkenyl or alkynyl group, the substituent or substituents may have for example any of the values recited above for substituents in the definition of $R^1$ when $R^1$ is an alkyl, alkenyl or alkynyl group. When $R^3$ is a substituted alkyl, alkenyl, alkynyl or phenyl group, the substituent or substituents may have for example any of the values recited in the definition of $R^1$ above when $R^1$ is an ester radical. When $R^3$ is an acyl radical it may for example be an alkanesulphonyl radical (e.g. a $C_1-C_6$ alkanesulphonyl radical) or an alkanoyl radical (e.g. a formyl radical or a $C_2-C_6$ alkanoyl radical). When the groups $R^2$ and $R^3$, together with the nitrogen atom to which they are attached form a heterocyclic ring, the heterocyclic ring may be 5- or 6-membered and may for example be a pyrrolidine, piperidine, or morpholine ring, each of which may optionally bear one or more methyl substituents.

Within the sub-class of compounds in which R is a group $R^2R^3N-$, preferred compounds are those in which $R^2$ and $R^3$ are both alkyl groups, or in which the group $R^2R^3N-$ constitutes a heterocyclic ring.

When the group $R^6$ is an alkyl radical it may for example have from 1 to 12 carbon atoms, (e.g. 1 to 6 carbon atoms). When the group $R^6$ is an alkenyl or alkynyl radical it may have for example from 2 to 12 carbon atoms. Examples of substituents which may be present when $R^6$ is a substituted alkyl, alkenyl or alkynyl radical include those substituents recited above for the case when $R^1$ is a substituted alkyl radical.

Further examples of substituents for $R^6$ include carboxy, hydroxy, alkoxycarbonyl (e.g. containing 2 to 6 carbon atoms) and phosphonyl

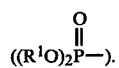

Particular examples of compounds according to the invention include those listed in Table 1 below:

TABLE I

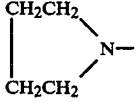

| COMPOUND NUMBER | R | R⁴ | R⁵ | Melting Point °C. |
|---|---|---|---|---|
| 1 | HO | H | H | |
| 2 | HO | H | isoPrNH$_3^+$ | 165 |
| 3 | HO | 4-CH$_3$O.C$_6$H$_4$.NH$_3^+$ | 4-CH$_3$O.C$_6$H$_4$.NH$_3^+$ | 231–233 |
| 4 | CH$_3$O | H | isoPrNH$_3^+$ | 129–131 |
| 5 | C$_2$H$_5$O | H | H | 144–145 |
| 6 | C$_2$H$_5$O | H | isoPrNH$_3^+$ | 158–160 |
| 7 | isoPrO | H | isoPrNH$_3^+$ | 161–163 |
| 8 | nPrO | H | isoPrNH$_3^+$ | 123–125 |
| 9 | —OCH$_2$.CH=CH$_2$ | H | isoPrNH$_3^+$ | 105–108 |
| 10 | NH$_2$ | H | H | 195–196 |
| 11 | CH$_3$NH | H | H | 111–112 |
| 12 | (CH$_3$)$_2$N— | H | H | oil |
| 13 | nPrNH— | H | H | 112–113 |
| 14 | nC$_6$H$_{13}$NH | H | H | 191–192 |
| 15 | C$_6$H$_5$NH | H | H | 214–215 |
| 16 | $\begin{array}{c}CH_2CH_2\\ \phantom{CH_2}\diagdown\\ \phantom{CH_2CH_2}N—\\ \phantom{CH_2}\diagup\\ CH_2CH_2\end{array}$ | H | H | 134–135 |
| 17 | HC≡CCH$_2$NH— | H | H | 205–206 |
| 18 | H$_2$C=CH—CH$_2$NH— | H | H | 206–207 |

Further Examples of compounds according to the invention include the following:

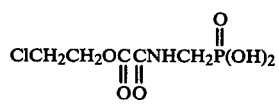

(m.p. 127–128° C.)

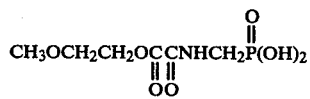

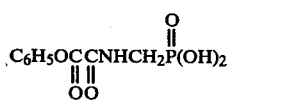

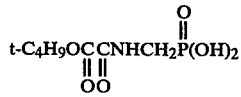

and salts and esters thereof; that is to say compounds in which one or both of the hydrogen atoms of the

group are replaced by a cation as defined above, or in which one of the hydrogen atoms of the

group is replaced by an ester radical as defined above and the remaining hydrogen atom is optionally replaced by a cation.

The compounds may be prepared by a variety of methods. One method of preparation of compounds in which R is an R$^1$O group is illustrated in outline in Scheme A below:

Scheme A (a) 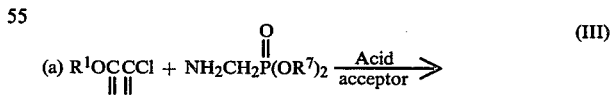 (III)

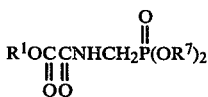

(b) (III) 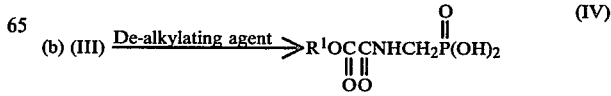 (IV)

-continued (c) (IV) + $\xrightarrow[\text{e.g. NaOH}]{\text{Hydrolysis}}$ 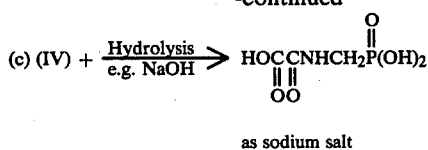

as sodium salt

According to Scheme A, an appropriate substituted carbonyl chloride $R^1OCOCOCl$ (eg. ethoxalyl chloride, $C_2H_5OCOCOCl$) is reacted with an ester of aminomethanephosphonic acid in the presence of an acid acceptor. The ester group $R^7$ may be for example an alkyl radical of 1 to 6 carbon atoms. Examples of acid acceptors include tertiary amines (eg. triethylamine, pyridine, and dimethylaniline) and alkali metal carbonates (eg. potassium carbonate). The reaction may be conducted at ambient temperature, or the reaction mixture may be cooled (eg. to 0°–5° C.) to moderate the vigour of the reaction if desired. Preferably the reaction is carried out in a solvent or diluent for the reactants. The product (III) may be isolated by standard methods.

The substituted carbonyl chlorides $R^1OCOCOCl$ used in Scheme A are in general known compounds. Where individual compounds have not previously been described in the chemical literature, they may be prepared by methods analogous to those used to prepare the known compounds. Esters of aminomethylphosphonic acid are also known compounds, as is aminomethylphosphonic acid itself.

In Stage (b) of Scheme A, the ester groups $R^7$ of the phosphonic acid part of the molecule (III) are removed. This may be carried out, for example, by treating the ester (III) with trimethylsilyl bromide or iodide. The trimethylsilyl iodide may be generated in situ by using a mixture of hexamethyldisilane and iodine or trimethylsilylchloride and sodium iodide. The reaction is preferably carried out in an aprotic diluent or solvent (eg. acetonitrile) for the reactants.

The reaction may be accelerated by heating, for example to a temperature in the range from 50°–120°, eg. 70°–100°. The reaction mixture is then treated with water and the phosphonic acid derivative (IV) isolated by standard methods. Thus the reaction after dilution with water may be extracted with a water-immiscible organic solvent, and the water layer then separated and evaporated to give the phosphonic acid derivative (IV) which may be further purified if required.

In Stage (c) of Scheme A, the carboxylic ester group is hydrolysed. Preferably alkaline hydrolysis under mild conditions is used, for example treatment with an alkali metal hydroxide in aqueous solution at room temperature. The sodium salt may be recovered by evaporation of the aqueous solution under reduced pressure. The free acid itself (i.e. N-(carboxycarbonyl)aminomethylphosphonic acid) may be isolated by passing the sodium salt of the acid as an aqueous solution through a bed of an ion exchange resin in acid form, and evaporating the eluate.

Compounds of the invention in which R is an $R^2R^3N$— group may be prepared by reaction of an oxamoyl chloride $R^2R^3NCOCOCl$ with an aminomethylphosphonic ester in the presence of an acid acceptor, followed by removal of the ester groups from the phosphonic acid part of the molecule, following the method described in Stages (a) and (b) of Scheme A for the compounds in which R is an $R^1O$ group.

A further method of preparing compounds of the invention is outlined in Scheme B below:

Scheme B

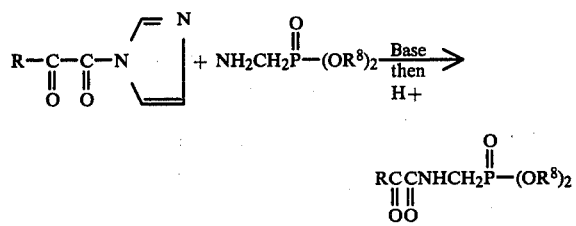

In this Scheme, R is as prevously defined and each group $R^8$ is hydrogen, a cation, or an alkyl group e.g. a $C_1$–$C_6$ alkyl group.

In Scheme B, an acylimidazole derivative is reacted with aminomethylphosphonic acid or an ester thereof in presence of a base. The reaction is preferably carried out in a solvent or diluent which is inert towards the reactants and usually proceeds at ambient temperature. The base may be for example a tertiary amine (e.g. triethylamine). The acyl imidazole compounds are either known or may be prepared by conventional methods. When both groups $R^8$ are alkyl groups it will be necessary to de-esterify the product of the reaction by treatment with for example trimethylsilyl iodide as described above.

A further method of preparing compounds according to the invention is outlined in Scheme C below:

Scheme C

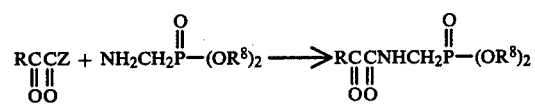

In Scheme C, each group $R^8$ stands for hydrogen, a cation, or an alkyl group (e.g. an alkyl group of 1 to 6 carbon atoms) and Z stands for an alkoxy group (e.g. an alkoxy group of 1 to 6 carbon atoms) or an optionally substituted phenoxy group. The reaction is preferably carried out in a solvent or diluent which is inert towards the reactants, and may be accelerated by heating, for example to a temperature in the range 50°–150° C. Where both groups $R^8$ are alkyl groups, it is necessary to treat the product of Scheme C with a de-alkylating agent, for example trimethylsilyl iodide, as described above, to obtain a compound according to the invention.

In the case where R stands for a group $R^1O$, a compound having a particular group $R^1O$ may be converted into a compound having a different group $R^1O$ by transesterification. Thus for example, a compound in which $R^1O$ stands for an ethoxy group may be converted to a compound in which $R^1O$ is a methoxy group by heating with an excess of methanol as shown in Scheme D below:

Scheme D

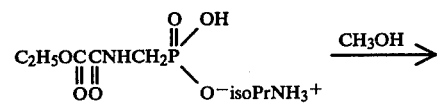 $\xrightarrow{\text{CH}_3\text{OH}}$

-continued

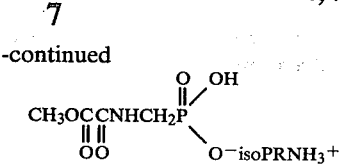

The process may conveniently be carried out when the phosphonic acid residue is in the form of a salt. In Scheme D, the isopropylamine salt is shown, but other salts may be employed. In general, the compound which is to be converted is heated (e.g. to a temperature in the range 50°–150° C.) with an excess of the alcohol $R^1OH$ which is to supply the new group $R^1O$. A fairly lengthy period of heating (e.g. 12 hours or more) may be required. The product is isolated by removing the excess of the alcohol $R^1OH$ and further purified if desired.

Compounds of formula (II) according to the invention may be prepared by treatment of compounds of formula (I) under basic conditions with a halide $R^6X$ wherein X is chlorine, bromine or iodine.

When the group $R^6$ is hydrogen, the compounds represented by formula (I) and (II) are tautomers of one another; it may be expected that in any particular case the compounds exist essentially as represented by formula (I) but that there may be a small proportion of the compound of formula (II) in dynamic equilibrium with the tautomer of formula (I).

In another aspect the invention provides a process of inhibiting the growth of unwanted plants, which comprises applying to the plants, or to the locus thereof, a phytotoxic amount of a compound of the formula (I) or (II) as hereinbefore defined. The compounds of the invention are herbicidally active against a wide range of mono- and di-cotyledonous plants including perennials.

The rate at which the compounds are to be applied in the process of the invention may vary, depending for example upon the identity of the particular compound chosen for use and the plant species whose growth is to be inhibited, but in general amounts of from 0.1 to 10.0 kilograms per hectare (eg. 0.1 to 2.0 kg hectare) will be suitable. Application rates down to 0.03 kg/ha have proved effective on some species. The skilled worker in the herbicidal art will be able to establish appropriate application rates by standard procedures without undue experimentation.

The compounds used in the process of the invention are preferably applied in the form of a composition, in which the active ingredient is mixed with a carrier comprising a solid or liquid diluent. In another aspect, therefore, the invention provides a herbicidal composition, comprising as an active ingredient a compound of the formula (I) as hereinbefore defined, in admixture with a solid or liquid diluent. Preferably the composition also comprises a surface-active agent.

The solid compositions of the invention may be for example, in the form of dusting powders, or may take the form of granules. Suitable solid diluents include, for example, kaolin, bentonite, kieselguhr, dolomite, calcium carbonate, talc, powdered magnesia, and Fuller's earth.

Solid compositions may also be in the form of dispersible powders or grains comprising in addition to the active ingredient, a wetting agent to facilitate the dispersion of the powder or grains in liquids. Such powders or grains may include fillers, suspending agents and the like.

Liquid compositions include aqueous solutions, dispersions and emulsions containing the active ingredient preferably in the presence of one or more surface active agents. Water or organic liquids may be used to prepare solutions, dispersions, or emulsions of the active ingredient. The liquid compositions of the invention may also contain one or more corrosion inhibitors for example lauryl isoquinolinium bromide.

Surface active agents may be of the cationic, anionic or non-ionic type. Suitable agents of the cationic type include for example quaternary ammonium compounds, for example cetyltrimethyl ammonium bromide. Suitable agents of the anionic type include for example soaps, salts of aliphatic mono-esters of sulphuric acid, for example sodium lauryl sulphate; and salts of sulphonated aromatic compounds, for example dodecyl-benzenesulphonate, sodium, calcium and ammonium lignosulphonate, butylnaphthalene sulphonate, and a mixture of the sodium salts of diisopropyl- and triisopropyl-naphthalenesulphonic acid. Suitable agents of the non-ionic type include, for example, the condensation products of ethylene oxide with fatty alcohols such as oleyl alcohol and cetyl alcohol, or with alkyl phenols such as octylphenol, nonylphenol, and octylcresol. Other non-ionic agents are the partial esters derived from long chain fatty acids and hexitol anhydrides, for example sorbitol monolaurate; the condensation products of the said partial esters with ethylene oxide and the lecithins.

Still further examples of non-ionic agents include the ethylene oxide condensates of long chain primary-amines, for example tallow amine (which comprises mainly $C_{16}$–$C_{18}$ primary aliphatic amines) condensed with 20 molar proportions of ethylene oxide.

The compositions which are to be used in the form of aqueous solutions, dispersions or emulsions are generally supplied in the form of concentrate containing a high proportion of the active ingredient, the concentrate being diluted with water before use. These concentrates are usually required to withstand storage for prolonged periods and after such storage to be capable of dilution with water in order to form aqueous preparations which remain homogenous for a sufficient time to enable them to be applied by conventional spray equipment.

The compositions of the invention may contain, in addition to carriers and surface-active agents, various other constituents to increase their usefulness. They may contain, for example, buffering salts to maintain the pH of the composition within a desired range; antifreeze agents, for example urea or propylene glycol; adjuvants, for example oils and humectants; and sequestrants, for example citric acid and ethylenediaminetetracetic acid, which help to prevent the formation of insoluble precipitates when the compositions are diluted with hard water. Aqueous dispersions may contain anti-settling agents and anti-caking agents. The compositions may in general contain a dye or pigment to impart a characteristic colour. Agents for increasing viscosity may be added to reduce the formation of fine droplets during spraying, and thereby reduce spray drift. Other additives useful for particular purposes will be known to those skilled in the formulation art.

In general concentrates may conveniently contain from 10 to 85% and preferably from 25 to 60% by weight of active ingredient. Dilute preparations ready for use may contain varying amounts of the active ingredient, depending upon the purpose for which they are to be used; however, dilute preparations suitable for many purposes contain between 0.01% and 10% and preferably between 0.1% and 1% by weight of the active ingredient.

The compounds of the invention can be used in association (for example in the form of a mixture) with another herbicide.

Examples of such herbicides are:

A. benzo-2,1,3-thiadiazin-4-one-2,2-dioxides such as 3-isopropylbenzo-2,1,3-thiadiazin-4-one-2,2-dioxide (bentazon);

B. hormone herbicides, particularly the phenoxy alkanoic acids such as 4-chloro-2-methylphenoxy acetic acid (MCPA), 2-(2,4-dichlorophenoxy)propionic acid (dichlorprop), 2,4,5-trichlorophenoxyacetic acid (2,4,5-T), 4-(4-chloro-2-methylphenoxy)butyric acid (MCPB), 2,4-dichlorophenoxyacetic acid (2,4-D), 4-(2,4-dichlorophenoxy)butyric acid (2,4-DB), 2-(4-chloro-2-methylphenoxy)propionic acid (mecoprop), and their derivatives (e.g. salts, esters and amides);

C. 3-[4-(4-halophenoxy)phenyl]-1,1-dialkylureas such as 3-[4-(4-chlorophenoxy)phenyl]-1,1-dimethylurea (chloroxuron);

D. dinitrophenols and their derivatives (e.g. acetates) such as 2-methyl-4,6-dinitrophenol (DNOC), 2-t-butyl-4,6-dinitrophenol (dinoterb), 2-secbutyl-4,6-dinitrophenol (dinoseb) and its ester, dinoseb acetate;

E. dinitroaniline herbicides such as N',N'-diethyl-2,6-dinitro-4-trifluoromethyl-m-phenylenediamine (dinitramine), 2,6-dinitro-N,N-dipropyl-4-trifluoromethylaniline (trifluralin) and 4-methylsulphonyl-2,6-dinitro-N,N-dipropylaniline (nitralin);

F. phenylurea herbicides such as N'-(3,4-dichlorophenyl)-N,N-dimethylurea (diuron) and N,N-dimethyl-N'-[3-(trifluoromethyl)phenyl]urea (flumeturon);

G. phenylcarbamoyloxyphenylcarbamates such as 3-[methoxycarbonylamino]phenyl (3-methylphenyl)carbamate (phenmedipham) and 3-[ethoxycarbonylamino]phenyl phenylcarbamate (desmedipham);

H. 2-phenylpyridazin-3-ones such as 5-amino-4-chloro-2-phenylpyridazin-3-one (pyrazon);

I. uracil herbicides such as 3-cyclohexyl-5,6-trimethyleneuracil (lenacil), 5-bromo-3-sec-butyl-6-methyluracil (bromacil) and 3-t-butyl-5-chloro-6-methyluracil terbacil);

J. triazine herbicides such as 2-chloro-4-ethylamino-6-(i-propylamino)-1,3,5-triazine (atrazine), 2-chloro-4,6-di(ethylamino)-1,3,5-triazine (simazine) and 2-azido-4-(i-propylamino)-6-methylthio-1,3,5-triazine (aziprotryne);

K. 1-alkoxy-1-alkyl-3-phenylurea herbicides such as 3-(3,4-dichlorophenyl)-1-methoxy-1-methylurea (linuron), 3-(4-chlorophenyl)-1-methoxy-1-methylurea (monolinuron) and 3-(4-bromo-4-chlorophenyl)-1-methoxy-1-methylurea (chlorobromuron);

L. thiolcarbamate herbicides such as S-propyl dipropylthiocarbamate (verolate);

M. 1,2,4-triazin-5-one herbicides such as 4-amino-4,5-dihydro-3-methyl-6-phenyl-1,2,4-triazine-5-one (metamitron) and 4-amino-6-t-butyl-4,5-dihydro-3-methylthio-1,3,4-triazin-5-one (metribuzin);

N. benzoic acid herbicides such as 2,3,6-trichlorobenzoic acid (2,3,6-TBA), 3,6-dichloro-2-methoxybenzoic acid (dicamba) and 3-amino-2,5-dichlorobenzoic acid (chloramben);

O. anilide herbicides such as N-(butoxymethyl)-2-chloro-2',6'-diethylacetanilide (butachlor), the corresponding N-methoxy compound (alachlor), the corresponding N-i-propyl compound (propachlor) and 3',4'-dichloropropionanilide (propanil);

P. dihalobenzonitrile herbicides such as 2,6-dichlorobenzonitrile (dichlobenil), 3,5-dibromo-4-hydroxybenzonitrile (bromoxynil) and 3,5-diiodo-4-hydroxybenzonitrile (ioxynil).

Q. haloalkanoic herbicides such as 2,2-dichloropropionic acid (dalapon), trichloroacetic acid (TCA) and salts thereof;

R. diphenylether herbicides such as 4-nitrophenyl 2-nitro-4-trifluoromethylphenyl ether (fluorodifen), methyl 5-(2,4-dichlorophenoxy)-2-nitrobenzoate (bifenox), 2-nitro-5-(2-chloro-4-trifluoromethylphenoxy)benzoic acid, 2-chloro-4-trifluoromethylphenyl 3-ethoxy-4-nitrophenyl ether and the compounds of European Patent Specification Publication No. 3416 (the disclosure of which Specification is incorporated herein by reference); and S. miscellaneous herbicides including N,N-dimethyldiphenylacetamide (diphenamid), N-(1-naphthyl)-phthalamic acid (naptalam) and 3-amino-1,2,4-triazole.

T. bipyridylium herbicides such as those in which the active entity is the 1,1'-dimethyl-4,4'-dipyridylium ion (paraquat) and those in which the active entity is the 1,1'-ethylene-2,2'-dipyridylium ion (diquat).

U. Aryloxyphenoxypropionic acids and their derivatives (salts, esters, amides, and the like).

Examples of such acids are:

2-[4-(5-trifluoromethylpyridyl-2-oxy)phenoxy]propionic acid.

2-[4-(4-trifluoromethylphenoxy)phenoxy]propionic acid.

2-[4-(2,4-dichlorophenoxy)phenoxy]propionic acid.

2-[4-(6-chlorobenzoxazolyl-2-oxy)phenoxy]propionic acid 4-methyl-4-(4-trifluoromethylphenoxy)phenoxybut-2-enoic acid.

The invention is illustrated by the following Examples in which, unless otherwise stated, all parts are by weight and all temperatures are in degrees Celsius.

EXAMPLE 1

This Example illustrates the preparation of N-(carboxycarbonyl)aminomethylphosphonic acid (Compound No. 1 of Table 1) having the structure

in the form of a sodium salt and also as the free acid.

Ethoxalyl chloride (2.73 g) in dry ethyl acetate (10 ml) was added with stirring to a solution of diethyl aminomethylphosphonate (3.34 g) and triethylamine (2.02 g) in dry ethyl acetate (20 ml) kept at 0°–5° by cooling in an ice bath. The reaction mixture was allowed to warm to ambient temperature. After three hours the mixture was filtered and the residue washed with ethyl acetate. The filtrate and washings were evaporated under reduced pressure to give a brown oil which was distilled under a pressure of 0.13 Torr at an air-bath temperature of 120°–140° C. to give a pale yellow oil (3.54 g).

The ester (III, R=$C_2H_5$, $R^3$=$C_2H_5$) so obtained (1.0 g) was taken up in dry acetonitrile (15 ml) and a stream of propene passed through the solution. Hexamethyldisilane (0.94 g) was added, followed by iodine (1.63 g).

The mixture was heated under reflux for 6 hours, allowed to cool overnight, and then heated under reflux for a further 8 hours. The solvent was removed under reduced pressure and the residue taken up in water (20 ml). The solution was washed with dichloromethane (4×10 ml, 4×5 ml). The aqueous solution was then evaporated to give a solid (0.72 g). Trituration with acetone gave a white solid which was washed with acetone and allowed to dry. The yield of N-(ethoxycarbonylcarbonyl)aminomethylphosphonic acid (Compound No. 5 of Table 1) was 0.43 g and the compound had a melting point of 144°–145° C.

Found: C, 28.25; H, 4.62; N, 6.72 $C_5H_{10}NO_6P$; requires: C, 28.4; H, 4.74; N, 6.64%.

A quantity (1.80 g) of the phosphonic acid derivative so prepared was added to sodium hydroxide (0.68 g) in water (10 ml) and the resulting solution stirred at room temperature for 4 hours. A sample of the solution was evaporated under reduced pressure to give a white solid. This was dissolved in deuterium oxide and was examined by nuclear magnetic resonance (NMR) spectroscopy. It was seen that hydrolysis of the ethyl ester was incomplete. Accordingly, a further amount (0.34 g) of sodium hydroxide dissolved in a little water was added to the reaction solution. The solution was stirred for a further four hours and then evaporated under reduced pressure. The residue, a frothy white solid, was triturated with acetone and the resulting suspension filtered to give a white solid identified as the sodium salt of N-(carboxycarbonyl)aminomethylphosphonic acid. A sample (0.2 g) of this material was converted to N-(carboxycarbonyl)aminomethylphosphonic acid by passing an aqueous solution of it down a column of Dowex 50W-X8 ion exchange resin in the acid form (Dowex 50W-X8is a Trade Mark for an ion exchange resin comprising a co-polymer of styrene and divinylbenzene with nuclear sulphonic acid groups), and collecting the portion of the eluate which was strongly acid. Evaporation gave the acid (0.12 g). A sample of this was dissolved in deuterium oxide and examined by NMR spectroscopy. The spectrum was consistent with the structure assigned; thus the $^{13}C$ spectrum showed a doublet (J=150 Hz) corresponding to the methylene group adjacent to the phosphorus atom, a doublet (J=4 Hz) corresponding to the ketonic CO group, and a singlet corresponding to the carboxylic CO group.

EXAMPLE 2

This Example illustrates a preparation of the monoisopropylamine salt of N-carboxycarbonyl-aminomethylphosphonic acid.

N-(Carboxycarbonyl)aminomethylphosphonic acid (Compound 1 of Table 1, 0.5 g), dissolved in water (5 ml) was treated with isopropylamine (0.156 g). The solution was stirred for one hour and the water removed under reduced pressure. Trituration with a little dry acetone gave the isopropylamine salt (Compound 2 of Table 1) as a white solid (0.62 g).

The di-p-methoxyaniline salt of N-(carboxycarbonyl)aminomethylphosphonic acid (Compound no. 3 of Table 1) was similarly prepared, using two molar proportions of p-methoxyaniline in place of isopropylamine.

EXAMPLE 3

This Example illustrates a preparation of the monoisopropylamine salt of N-(methoxycarbonylcarbonyl)-aminomethylphosphonic acid.

The mono-isopropylamine salt of N-(ethoxycarbonylcarbonyl)aminomethylphosphonic acid (Compound 6 of Table 1, 1.5 g) was heated under reflux in methanol (15 ml) for 12 hours. The solution was evaporated to a volume of about 5 ml and then diluted with ether until it became slightly cloudy. The solution was left overnight. The crystals which separated were washed with ether and dried, giving Compound No. 4 of Table 1 (0.53 g) with a melting point of 129°–131° C. Compound 8 was similarly prepared, using n-propanol in place of methanol.

EXAMPLE 4

This Example illustrates a method of preparing N-(ethoxycarbonylcarbonyl)aminomethylphosphonic acid (Compound 5 of Table 1) different from that illustrated in Example 1.

Aminomethylphosphonic acid (0.56 g) was suspended with stirring in dimethylformamide, and two molar proportions of triethylamine added (1.01 g). The minimum amount of water required to produce a clear solution (2 ml) was then added. A solution of N-(ethoxycarbonylcarbonyl)imidazole (1.0 g; 1.2 molar proportions) in dry dimethylformamide (5 ml) was then added dropwise with stirring. The resulting mixture was stirred at room temperature for 2 hours and the solvents then removed under reduced pressure. The semi-solid residue was triturated with chloroform. The white solid which resulted was collected and dried. The proton magnetic resonance spectrum of the product indicated that it contained a mixture of 2 parts of N-(ethoxycarbonylcarbonyl)aminomethylphosphonic acid with 1 part of aminomethylphosphonic acid, both acids being present as imidazole salts. High pressure liquid chromatography using reference samples of these compounds confirmed this identification of the product.

Mono-ethyl N-(ethoxycarbonylcarbonyl)aminoethylphosphate was prepared following the above procedure but using mono-ethyl aminoethylphosphonate hydrochloride as starting material.

EXAMPLE 5

This Example illustrates a preparation of the monoisopropylamine salt of N-(ethoxycarbonylcarbonyl)-aminomethylphosphonic acid.

Diethyl N-(ethoxycarbonylcarbonyl)aminomethylphosphonate (15.0 g prepared as described in Example 1) in dry dichloromethane (90 ml) was placed in a flask which was sealed with a rubber septum. Trimethylsilyl bromide (28 ml); ca. 3.8 molar proportions was added by syringe through the septum and the mixture stirred for four hours at room temperature. The solution was then evaporated under reduced pressure to give a yellow oil. This was taken up in dry dichloromethane (ca. 100 ml) and treated with ethanol (20 ml) to decompose the intermediate trimethylsilyl ester. The solution was then evaporated under reduced pressure to leave a yellowish semi-solid residue. Trituration of this with ethanol (ca. 8 ml) gave N-(ethoxycarbonylcarbonyl)aminomethylphosphonic acid as a white solid (6.82 g). A sample of acid prepared in this way (40 g) was taken up in ethanol (1500 ml) to give a slightly cloudy solution. To this isopropylamine (10.8 g, one molar proportion) was added dropwise with stirring. When addition was complete, the mixture was stirred for 2 hours and then evaporated under reduced pressure. The remaining viscous brown oil was taken up in warm ethanol (50 ml) and the solution diluted with ether until slightly cloudy.

On standing, a white solid separated. This was collected and washed with ethanol (ca. 50 ml) and then ether, giving Compound no. 6 Table 1 (48.7 g). A sample recrystallised from ethanol (50 ml) plus water (3 ml) had a melting point of 158°–160°.

EXAMPLE 6

This Example illustrates a preparation of the monoisopropylamine salt of N-(isopropoxycarbonylcarbonyl)aminomethylphosphonic acid (Compound no. 7 of Table 1).

Diethyl N-(isopropoxycarbonylcarbonyl)aminomethylphosphonate (2.81 g) in dry dichloromethane (10 ml) was placed in a flask which was sealed with a rubber septum. Trimethylsilyl bromide (6.12 g; four molar proportions) was added by syringe. The resulting solution was stirred for four hours at room temperature and then evaporated under reduced pressure. The residue was taken up in dry dichloromethane (10 ml) and treated with isopropanol (5 ml) to decompose the trimethylsilyl ester. Evaporation under reduced pressure gave a viscous orange oil. This was dissolved in isopropanol (5 ml) and isopropylamine (0.57 g) was added. The solution was stirred for one hour and then evaporated under reduced pressure. Trituration of the residue with acetone gave Compound no. 7 of Table 1 as a white powder (1.52 g) with a melting point of 161°–163°.

Compound 9 of Table 1 was prepared by a similar procedure using diethyl N-(allyloxycarbonylcarbonyl)aminomethyl phosphonate as starting material in place of diethyl N-(isopropoxycarbonylcarbonyl)aminomethylphosphonate. The starting material for this Example and for Compound 9 were prepared respectively from the reaction is isopropoxalyl chloride, and allyloxalyl chloride respectively, with diethyl aminomethyl phosphonate, following the procedure described in Example 1 for the preparation of diethyl N-(ethoxycarbonylcarbonyl)aminomethyl phosphonate from the reaction of ethoxalyl chloride with diethyl aminomethylphosphonate.

EXAMPLE 7

This Example illustrates a method of preparing Compound 10 of Table 1.

Step (a): Reaction with ammonia

Diethyl N-(ethoxycarbonylcarbonyl)aminomethyl phosphonate (6.8 g) was stirred with concentrated ammonia solution (d 0.88, 30 ml) overnight. The precipitate which formed was washed with water (2×30 ml) and dried with chloroform (2×30 ml) and dried to give diethyl N-(carbamoylcarbonyl)aminomethyl phosphonate (4.14 g) with a melting point of 165°–167°.

Step (b): Hydrolysis of phosphonic ester

The amide-ester so prepared (4.0 g) in dry acetonitrile (20 ml) was treated with 4 molar proportions of trimethylsilyl bromide and the mixture stirred at room temperature for 3 hours. The solvent was then removed under reduced pressure and the residue treated with acetonitrile (10 ml) and ethanol (20 ml). The solvent was again evaporated under reduced pressure and the residue recrystallised from a mixture of methanol and ether to give N-(carbamoylcarbonyl)aminomethylphosphonic acid (Compound 10 of Table 1; 2 g) with a melting point of 195°–196°.

EXAMPLE 8

This Example illustrates a method of preparing Compounds 11 to 16 of Table 1 by reaction of an appropriate amine with diethyl N-(ethoxycarbonyl)aminomethyl phosphonate, and subsequent removal of the phosphonic ester groups by treatment with trimethylsilyl bromide. In the case of Compounds 11 to 14, an equimolar amount of the amine was left to stand with the diethyl N-(ethoxycarbonylcarbonyl)aminomethyl phosphonate in ethanol solution at room temperature overnight and the solvent then removed under reduced pressure. The residue was then recrystallized from chloroform-hexane. In the case of Compound 15, the diethyl N-(ethoxycarbonylcarbonyl)aminomethyl phosphonate was heated with an equimolar amount of aniline at 160° for 4 hours and the product recrystallised from chloroform/hexane. In the case of Compound 16, the phosphonate ester was heated at 80° C. for 4 hours with an equimolar amount of pyrrolidine, and the product then recrystallised from chloroform/hexane. The melting points of these amide-esters are given in the Table below. Melting points of amide-ester

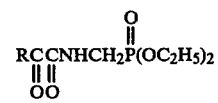

| R | Melting point °C. |
|---|---|
| CH$_3$NH— | 89–90 |
| (CH$_3$)$_2$N— | oil |
nC$_3$H$_7$NH— | 84–85 |
| nC$_6$H$_{13}$NH— | 66–67 |
| C$_6$H$_5$NH | 77–78 |
| 1-pyrrolidinyl | 67–69 |

The structure of the dimethylamino compound which was an oil at room temperature, was confirmed by its infra-red and nuclear magnetic resonance spectra. The elemental analysis of each compound was consistent with the structure assigned.

The amide-esters were converted to compounds 11 to 16 of Table 1 by treatment with trimethylsilyl bromide following the procedure described in Step (b) of Example 7, but using dichloromethane as the solvent rather than acetonitrile.

EXAMPLE 9

This Example illustrates the herbicidal activity of N-(ethoxycarbonylcarbonyl)aminomethylphosphonic acid, (Compound no. 5 of Table 1).

The compound (0.07 g) was formulated for test by mixing it with 0.7 ml of a solution containing a mixture of 1 part Tween 85 to 2 parts of Synperonic NPE 1800 dissolved in cyclohexanone, the concentration of the solution being 5 grams of the mixture per 100 ml of cyclohexanone. Tween 85 is a Trade Mark for a surface-active agent comprising a condensate of sorbitan trioleate with 20 molar proportions of ethylene oxide. Synperonic NPE 1800 is a Trade mark for a surface-active agent comprising a condensate of p-nonylphenol, propylene oxide, and ethylene oxide. The mixture of the compound with the cyclohexanone solution was shaken with glass beads and diluted to 7 ml with water.

The spray composition so prepared was sprayed on to young pot plants (post-emergence test) of the species named in Table 1 below, at a rate equivalent to 1000 liters per hectare (10 kilograms of test compound per hectare). Damage to plants was assessed 14 days after spraying, by comparison with untreated plants, on a scale of 0 to 3, where 0 is no effect and 3 represents 75 to 100% kill. In a test for pre-emergence herbicidal activity, seeds of the test species were placed on the surface of plastic trays of soil and were sprayed with the composition prepared as described above at the rate of 1000 liters per hectare. The seeds were then covered with further soil. Three weeks after spraying, the seedlings in the sprayed trays were compared with the seedlings in unsprayed control trays, the damage being assessed on the same scale of 0 to 3. The results are given in Table 2 below.

TABLE 2

| Pre- or Post-Emergence Application | Test Plants | | | | | |
|---|---|---|---|---|---|---|
| | Lt | To | Av | St | Ll | Cn |
| Pre | 0 | 1 | 1 | 3 | 2 | 3 |
| Post | 3 | 3 | 3 | 3 | 3 | 3 |

Names of Test Plants
Lt Lettuce
To Tomato
Av *Avena fatua*
St *Setaria viridis*
Ll *Lolium perenne*
Cn *Cynodon rotundus*

EXAMPLE 10

This Example illustrates the herbicidal activity of compounds 2, 3 and 7 of Table 1. The compounds were tested according to the procedure described in Example 9. The results are given in the Table below.

| COMPOUND NUMBER | APPLICATION Rate kg/ha | PRE- OR POST EMERGENCE APPLICATION | TEST PLANTS | | | | | |
|---|---|---|---|---|---|---|---|---|
| | | | Lt | To | Av | St | Ll | Cn |
| 2 | 4 | Post | 1 | 2 | 2 | 3 | 0 | 3 |
| 3 | 4 | Pre | 1 | 0 | 2 | 3 | 2 | 3 |
| | | Post | 3 | 3 | 3 | 3 | 2 | 3 |
| 7 | 4 | Pre | 2 | 0 | 3 | 3 | 3 | 3 |
| | | Post | 3 | 3 | 3 | 3 | 3 | 3 |

EXAMPLE 11

This Example illustrates the herbicidal properties of compounds of Table 1. The compounds were submitted to herbicide tests as described below.

Each compound was formulated for test by mixing an appropriate amount of it with 5 ml of an emulsion prepared by diluting 160 ml of a solution containing 21.8 grams per liter of Span 80 and 78.2 grams per liter of Tween 20 in methylcyclohexanone to 500 ml with water. Span 80 is a Trade Mark for a surface-active agent comprising sorbitan monolaurate. Tween 20 is a Trade Mark for a surface-active agent comprising a condensate of 20 molar proportions of ethylene oxide with sorbitan monolaurate. The mixture of the compound and the emulsion was then shaken with glass beads and diluted to 40 ml with water. The spray compositions so prepared was sprayed on to young pot plants (post-emergence test) of the species named in the Table below, at a rate equivalent to 1000 liters per hectare. Damage to plants was assessed 14 days after spraying by comparison with untreated plants, on a scale of 0 to 5 where 0 is 0 to 20% damage and 5 is complete kill. In the Table of results, a dash (-) means that no test was made.

A test was also carried out to detect pre-emergence herbicidal activity. Seeds of the test species were placed on the surface of fibre trays of soil and were sprayed with the compositions at the rate of 1000 liters per hectare. The seeds were then covered with further soil. Three weeks after spraying, the seedlings in the sprayed fibre trays were compared with the seedlings in unsprayed control trays, the damage being assessed on the same scale of 0 to 5.

The results of the tests are given in the Table below.

| COMPOUND NO | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Sb | Rp | Ct | Sy | Mz | Ww | Rc | Sn | Ip | Am | Pi | Ca |
| 1 | 5 | Pre | 0 | 0 | 3 | 3 | 1 | 2 | 3 | — | 0 | — | — | 0 |
| | | Post | 4 | 2 | 4 | 1 | 1 | 3 | 1 | 3 | 3 | 3 | 3 | 2 |
| 4 | 4 | Pre | 3 | 1 | 0 | 3 | 1 | 2 | 4 | 2 | 2 | 1 | 0 | — |
| | | Post | 4 | 4 | 4 | 3 | 3 | 3 | 2 | 4 | 4 | 4 | — | 3 |
| 5 | 5 | Pre | 0 | 0 | 1 | 3 | 1 | 2 | 1 | 0 | 0 | — | — | 0 |
| | | Post | 3 | 1 | 2 | 2 | 1 | 4 | 1 | 3 | 3 | 2 | 3 | 2 |
| 6 | 4 | Pre | 2 | 2 | 1 | 4 | 0 | 3 | 4 | 0 | 2 | 0 | 0 | — |
| | | Post | 4 | 4 | 4 | 3 | 3 | 4 | 4 | 4 | 3 | 4 | — | 4 |
| 8 | 4 | Pre | 0 | 2 | 2 | 3 | 5 | 2 | 4 | 0 | 1 | 0 | 0 | 0 |
| | | Post | 5 | 4 | 4 | 3 | 3 | 3 | 4 | 4 | 4 | 4 | — | 3 |
| 12 | 4 | Pre | 3 | 1 | 0 | 3 | 1 | 2 | 4 | 2 | 2 | 1 | 0 | — |
| | | Post | 4 | 4 | 4 | 3 | 3 | 3 | 2 | 4 | 4 | 4 | — | 3 |

| COMPOUND NO | RATE OF APPLICATION kg/ha | PRE- OR POST-EMERGENCE APPLICATION | TEST PLANTS | | | | | | | | | | | |
|---|---|---|---|---|---|---|---|---|---|---|---|---|---|---|
| | | | Ga | Xa | Ab | Co | Av | Dg | Al | St | Ec | Sh | Ag | Cn |
| 1 | 5 | Pre | 1 | 0 | 0 | 1 | 3 | 1 | 2 | 4 | 1 | 3 | 5 | 5 |
| | | Post | 2 | 4 | 3 | 2 | 3 | 2 | 2 | 3 | 5 | 5 | 2 | 3 |
| 4 | 4 | Pre | 0 | 3 | 0 | 2 | 3 | 2 | 3 | 5 | 3 | 4 | 5 | 5 |
| | | Post | 3 | 3 | 4 | 4 | 4 | 4 | 2 | 5 | 4 | 4 | 4 | 4 |
| 5 | 5 | Pre | 0 | 0 | 0 | 0 | 1 | 0 | 1 | 3 | 1 | 3 | 3 | 5 |
| | | Post | 1 | 3 | 1 | 2 | 3 | 2 | 2 | 3 | 3 | 3 | 3 | 2 |
| 6 | 4 | Pre | 0 | 0 | 0 | 4 | 3 | 3 | 1 | 5 | 5 | 5 | 5 | 5 |
| | | Post | 3 | 4 | 4 | 4 | 3 | 4 | 2 | 4 | 4 | 4 | 4 | 4 |
| 8 | 4 | Pre | 0 | 4 | 2 | 3 | 3 | 3 | 4 | 5 | 3 | 5 | 5 | 5 |

|    |   |      |   |   |   |   |   |   |   |   |   |   |   |
|----|---|------|---|---|---|---|---|---|---|---|---|---|---|
|    |   | Post | 3 | 3 | 4 | 4 | 4 | 4 | 2 | 5 | 4 | 4 | 4 | 4 |
| 12 | 4 | Pre  | 0 | 3 | 0 | 2 | 3 | 2 | 3 | 5 | 3 | 4 | 5 | 5 |
|    |   | Post | 3 | 3 | 4 | 4 | 4 | 4 | 2 | 5 | 4 | 4 | 4 | 4 |

Names of test plants
Sb Sugar beet
Rp Rape
Ct Cotton
Sy Soya Bean
Mz Maize
Ww Winter Wheat
Rc Rice
Sn *Senecio vulgaris*
Ip *Ipomoea purpurea*
Am *Amaranthus retroflexus*
Pi *Polygonum aviculare*
Ca *Chenopodium album*
Ga *Galium aparine*
Xa *Xanthium spinosum*
Ab *Abutilon theophrasti*
Co *Cassia obtusifolia*
Av *Avenua fatua*
Dg *Digitaria sanguinalis*
Al *Alopecurus myosuroides*
St *Setaria viridis*
Ec *Echinochloa crus-galli*
Sh *Sorghum halepense*
Ag *Agropyron repens*
Cn *Cyperus rotundus*

EXAMPLE 12

This Example illustrates the herbicidal effects of compound 5, of Table 1 against certain perennial weed plants. The test plants were grown in plastic pots, in John Innes No. 1 compost for about 12 weeks, so that they had developed a well established underground system of rhizomes, stolons, or tubers. The compound under test was applied as a post-emergence spray to the foliage of the test plants, in a spray volume of 200 liters per hectare. A surfactant comprising a condensate of 20 molar proportions of ethylene oxide with tallow amine was incorporated in the spray solution at a concentration of 0.5 grams per 100 ml. In the case of Agropyron, and Sorghum the foliage was cut to a height of about 3 cm two weeks before spraying, so that spray was applied to vigorous new foliage. Three weeks after spraying, visual assessments of damage were made, on a scale of 0 to 9. The scale figures represent the following percentage damage to the plants:

| Scale Figure | Percentage Damage |
|---|---|
| 0 | 0–4 |
| 1 | 5–16 |
| 2 | 17–27 |
| 3 | 28–38 |
| 4 | 39–49 |
| 5 | 50–60 |
| 6 | 61–71 |
| 7 | 72–82 |
| 8 | 83–94 |
| 9 | 95–99 |
| X | Complete Kill |

The foliage was then cut off at soil level. In order to assess the extent to which the compound controlled regrowth from the underground parts of the plants, the regrowth was harvested after a further four weeks. The fresh weight of the regrowth was expressed as a percentage of the regrowth of untreated control plants.

The Table below gives the results of this test.

| Test Species | Application Rate kg/ha | Top Kill Score | Percentage Control |
|---|---|---|---|
| *Agropyron* | 0.25 | 1 | 0 |
| *repens* | 0.5 | 1 | 0 |
|  | 1.0 | 2 | 0 |
|  | 2.0 | 3 | 0 |
| *Cynodon* | 0.25 | 1 | 14 |
| *dactylon* | 0.5 | 2 | 70 |
|  | 1.0 | 3 | 74 |
|  | 2.0 | 3 | 79 |
| *Paspalum* | 0.25 | 3 | 0 |
| *conjugatum* | 0.5 | 4 | 70 |
|  | 1.0 | 4 | 98 |
|  | 2.0 | 6 | 100 |
| *Sorghum* | 0.25 | 4 | 0 |
| *halepense* | 0.5 | 6 | 46 |
|  | 1.0 | 7 | 59 |
|  | 2.0 | 9 | 89 |
| *Cirisium* | 0.25 | 1 | 4 |
| *aruense* | 0.5 | 5 | 50 |
|  | 1.0 | 7 | 100 |
|  | 2.0 | 7 | 100 |

I claim:

1. Substituted methylphosphonic acid derivatives of the formula:

$$R-C(=O)-C(=O)-NHCH_2-P(=O)(OR^4)(OR^5) \quad (I)$$

wherein R is (a) a group $R^1O$ wherein $R^1$ is hydrogen, a cation, or a hydrolyzable ester radical; or (b) a group $R^2R^3N-$ wherein $R^2$ is hydrogen or an alkyl, alkenyl, or alkynyl group each of which may optionally be substituted by halogen, alkoxy of 1 to 6 carbon atoms, alkylthio of 1 to 6 carbon atoms, or phenyl optionally substituted by one or more halogen atoms or $C_{1-6}$ alkoxy, $C_{1-6}$ alkyl, $C_{2-6}$ alkenyl, $CF_3$, $NO_2$, or $CN$ groups; $R^3$ may have any of the values recited for $R^2$ above or may additionally be a phenyl group or an acyl group; $R^4$ is hydrogen or cation; $R^5$ is hydrogen or a cation.

2. A compound as claimed in claim 1 wherein R is a group $R^1O$ wherein $R^1$ is
    (a) an alkyl group of 1 to 20 carbon atoms optionally substituted by halogen, alkoxy of 1 to 6 carbon atoms, alkylthio of 1 to 6 carbon atoms, or phenyl optionally substituted by one or more halogen atoms or $C_{1-6}$ alkoxy, $CF_3$, $NO_2$, CN, or $C_{1-6}$ alkyl or $C_{2-6}$ alkenyl groups;

(b) a cycloalkyl radical of 3 to 6 carbon atoms optionally substituted by any one or more of the substituents recited above for the case when $R^1$ is alkyl;

(c) an alkenyl or alkylnyl radical of 2 to 6 carbon atoms either of which may optionally be substituted with any one or more of the substituents recited above for the case when $R^1$ is alkyl; or (d) a phenyl radical optionally substituted by one or more $C_{1-6}$ alkyl, $C_{2-6}$ alkenyl, $C_{1-6}$ alkoxy, $C_{1-6}$ alkylthio, $C_{1-6}$ alkylsulphinyl, $C_{1-6}$ alkanesulphonyl, nitro, cyano, carboxy, carbamoyl, $C_{2-6}$ alkoxycarbonyl, or $CF_3$ groups, or atoms of fluorine, chlorine, bromine, or iodine.

3. A compound as claimed in claim 1 wherein R is a group $R^1O$ in which $R^1$ is an alkyl radical of 1 to 6 carbon atoms, $R^5$ is hydrogen, and $R^4$ is a cation.

4. A compound as claimed in claim 3 wherein $R^4$ is a monoalkylammonium cation.

* * * * *